(12) United States Patent
Gregerson et al.

(10) Patent No.: US 7,661,881 B2
(45) Date of Patent: *Feb. 16, 2010

(54) SYSTEMS AND METHODS FOR IMAGING LARGE FIELD-OF-VIEW OBJECTS

(75) Inventors: Eugene A. Gregerson, Bolton, MA (US); Richard K. Grant, Sudbury, MA (US); Norbert Johnson, North Andover, MA (US)

(73) Assignee: Medtronic Navigation, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/522,794

(22) Filed: Sep. 18, 2006

(65) Prior Publication Data

US 2007/0086566 A1  Apr. 19, 2007

Related U.S. Application Data

(63) Continuation of application No. 10/392,365, filed on Mar. 18, 2003, now Pat. No. 7,108,421.

(60) Provisional application No. 60/366,062, filed on Mar. 19, 2002.

(51) Int. Cl.
*H05G 1/04* (2006.01)

(52) U.S. Cl. .................................. 378/197; 378/196

(58) Field of Classification Search .................. 378/37, 378/196–198, 145–146, 55, 57, 64, 51, 21, 378/4–20, 189, 181; 250/559.05, 208.1
See application file for complete search history.

(56) References Cited

U.S. PATENT DOCUMENTS 2,818,510 A  12/1957  Verse (Continued)

FOREIGN PATENT DOCUMENTS

CN  1 032 188 C  7/1996

(Continued)

OTHER PUBLICATIONS

Hein, et al., "Double-Centering Method for Increasing Efficiency of Cone-Beam X-Ray CT Reconstruction," IEEE, p. 1728, 2002.

(Continued)

*Primary Examiner*—Hoon Song
(74) *Attorney, Agent, or Firm*—Hamilton, Brook, Smith & Reynolds, P.C.

(57) ABSTRACT

An imaging apparatus and related method comprising a source that projects a beam of radiation in a first trajectory; a detector located a distance from the source and positioned to receive the beam of radiation in the first trajectory; an imaging area between the source and the detector, the radiation beam from the source passing through a portion of the imaging area before it is received at the detector; a detector positioner that translates the detector to a second position in a first direction that is substantially normal to the first trajectory; and a beam positioner that alters the trajectory of the radiation beam to direct the beam onto the detector located at the second position. The radiation source can be an x-ray cone-beam source, and the detector can be a two-dimensional flat-panel detector array. The invention can be used to image objects larger than the field-of-view of the detector by translating the detector array to multiple positions, and obtaining images at each position, resulting in an effectively large field-of-view using only a single detector array having a relatively small size. A beam positioner permits the trajectory of the beam to follow the path of the translating detector, which permits safer and more efficient dose utilization, as generally only the region of the target object that is within the field-of-view of the detector at any given time will be exposed to potentially harmful radiation.

17 Claims, 16 Drawing Sheets

U.S. PATENT DOCUMENTS

| | | | |
|---|---|---|---|
| 3,549,885 A | 12/1970 | Andersson | |
| 3,617,749 A | 11/1971 | Massiot | |
| 4,200,799 A | 4/1980 | Saito | |
| 4,352,986 A | 10/1982 | Pfeiler | |
| 4,442,489 A | 4/1984 | Wagner | |
| 4,481,656 A | 11/1984 | Janssen et al. | |
| 4,636,952 A | 1/1987 | Crawford et al. | |
| 4,741,015 A | 4/1988 | Charrier | |
| 4,803,714 A | 2/1989 | Vlasbloem | |
| 4,810,881 A | 3/1989 | Berger et al. | |
| 4,817,121 A | 3/1989 | Shimizu et al. | |
| 4,829,252 A | 5/1989 | Kaufman | |
| 4,875,228 A | 10/1989 | Archer | |
| 4,884,293 A | 11/1989 | Koyama | |
| 4,935,949 A | 6/1990 | Fujita et al. | |
| 4,955,046 A | 9/1990 | Siczek et al. | |
| 4,982,415 A | 1/1991 | Shibata et al. | |
| 4,987,585 A | 1/1991 | Kidd et al. | |
| 5,014,292 A | 5/1991 | Siczek et al. | |
| 5,014,293 A * | 5/1991 | Boyd et al. | 378/197 |
| 5,032,990 A | 7/1991 | Eberhard et al. | |
| D323,386 S | 1/1992 | Perusek | |
| 5,084,908 A * | 1/1992 | Alberici et al. | 378/4 |
| 5,095,501 A | 3/1992 | Kobayashi | |
| 5,097,497 A | 3/1992 | Deucher et al. | |
| 5,159,622 A | 10/1992 | Sakaniwa et al. | |
| 5,187,659 A | 2/1993 | Eberhard et al. | |
| 5,265,610 A | 11/1993 | Darrow et al. | |
| 5,287,274 A | 2/1994 | Saint Felix et al. | |
| D345,606 S | 3/1994 | Perusek | |
| 5,319,693 A | 6/1994 | Eberhard et al. | |
| 5,390,112 A | 2/1995 | Tam | |
| 5,448,607 A | 9/1995 | McKenna | |
| 5,448,608 A | 9/1995 | Swain et al. | |
| 5,452,337 A | 9/1995 | Endo et al. | |
| 5,499,415 A | 3/1996 | McKenna | |
| 5,515,416 A | 5/1996 | Siczek et al. | |
| 5,583,909 A | 12/1996 | Hanover | |
| 5,592,523 A | 1/1997 | Tuy et al. | |
| 5,598,453 A | 1/1997 | Baba et al. | |
| 5,625,660 A | 4/1997 | Tuy | |
| 5,638,419 A | 6/1997 | Ingwersen | |
| 5,661,772 A | 8/1997 | Bär et al. | |
| 5,668,846 A | 9/1997 | Fox et al. | |
| 5,740,222 A | 4/1998 | Fujita et al. | |
| 5,740,224 A | 4/1998 | Müller et al. | |
| 5,745,545 A | 4/1998 | Hughes | |
| 5,784,428 A | 7/1998 | Schmidt | |
| 5,802,138 A | 9/1998 | Glasser et al. | |
| 5,912,943 A | 6/1999 | Deucher et al. | |
| RE36,415 E | 11/1999 | McKenna | |
| 6,041,097 A | 3/2000 | Roos et al. | |
| 6,113,264 A * | 9/2000 | Watanabe | 378/197 |
| 6,147,352 A | 11/2000 | Ashburn | |
| 6,169,780 B1 * | 1/2001 | Yoshimura et al. | 378/39 |
| 6,203,196 B1 * | 3/2001 | Meyer et al. | 378/197 |
| 6,212,251 B1 | 4/2001 | Tomura et al. | |
| 6,215,841 B1 | 4/2001 | Hsieh | |
| 6,285,733 B1 | 9/2001 | Proksa et al. | |
| 6,289,073 B1 | 9/2001 | Sasaki et al. | |
| 6,314,157 B1 | 11/2001 | Tachizaki | |
| 6,322,251 B1 | 11/2001 | Ballhaus et al. | |
| 6,324,246 B1 | 11/2001 | Ruimi | |
| 6,325,537 B1 * | 12/2001 | Watanabe | 378/197 |
| 6,374,937 B1 | 4/2002 | Galando et al. | |
| 6,396,898 B1 | 5/2002 | Saito et al. | |
| 6,435,715 B1 * | 8/2002 | Betz et al. | 378/197 |
| 6,442,235 B2 | 8/2002 | Koppe et al. | |
| 6,484,049 B1 | 11/2002 | Seeley et al. | |
| 6,487,267 B1 | 11/2002 | Wolter | |
| 6,496,558 B2 * | 12/2002 | Graumann | 378/39 |
| 6,519,312 B1 | 2/2003 | Tybinkowski et al. | |
| 6,546,068 B1 | 4/2003 | Shimura | |
| 6,580,777 B1 | 6/2003 | Ueki et al. | |
| 6,582,120 B2 | 6/2003 | Schomberg | |
| 6,590,953 B2 | 7/2003 | Suzuki | |
| 6,609,826 B1 | 8/2003 | Fujii et al. | |
| 6,614,871 B1 * | 9/2003 | Kobiki et al. | 378/197 |
| 6,619,840 B2 | 9/2003 | Rasche et al. | |
| 6,742,929 B2 | 6/2004 | Horbaschek | |
| 6,771,732 B2 | 8/2004 | Xiao et al. | |
| 6,845,144 B2 | 1/2005 | Nishide et al. | |
| 6,869,217 B2 | 3/2005 | Rasche et al. | |
| 6,940,941 B2 | 9/2005 | Gregerson et al. | |
| 6,990,170 B2 | 1/2006 | Sugihara et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,338,207 B2 | 3/2008 | Gregerson et al. | |
| 7,490,982 B2 | 2/2009 | Gregerson et al. | |
| 2001/0005410 A1 | 6/2001 | Rasche et al. | |
| 2002/0118793 A1 | 8/2002 | Horbaschek | |
| 2002/0154728 A1 | 10/2002 | Morita et al. | |
| 2002/0168053 A1 | 11/2002 | Schomberg | |
| 2003/0016791 A1 | 1/2003 | Ukita | |
| 2003/0072416 A1 | 4/2003 | Rasche et al. | |
| 2004/0170254 A1 | 9/2004 | Gregerson et al. | |
| 2004/0240603 A1 | 12/2004 | Cai et al. | |
| 2006/0120511 A1 | 6/2006 | Gregerson et al. | |
| 2007/0086566 A1 | 4/2007 | Gregerson et al. | |
| 2007/0104308 A1 | 5/2007 | Gregerson et al. | |
| 2008/0013691 A1 | 1/2008 | Gregerson et al. | |
| 2008/0212743 A1 | 9/2008 | Gregerson et al. | |

FOREIGN PATENT DOCUMENTS

| | | |
|---|---|---|
| DE | G 89 05 588.8 | 9/1990 |
| DE | 195 35 583 A1 | 3/1997 |
| DE | 198 39 825 C 1 | 7/1999 |
| DE | 199 27 953 A1 | 1/2001 |
| EP | 0 231 969 | 1/1987 |
| EP | 0 471 455 A2 | 2/1992 |
| EP | 0 564 292 A2 | 10/1993 |
| EP | 0 810 005 A2 | 12/1997 |
| EP | 1 090 585 A1 | 4/2001 |
| FR | 2 304 321 | 10/1976 |
| GB | 2 088 670 A | 6/1982 |
| JP | 04-059893 B | 9/1990 |
| JP | 03-176033 | 7/1991 |
| JP | 07-250829 | 10/1995 |
| JP | 08-112277 | 5/1996 |
| JP | 09-304303 | 11/1997 |
| JP | 2000-070255 | 3/2000 |
| JP | 2000-197627 | 7/2000 |
| JP | 2000-312674 A | 11/2000 |
| JP | 2001-008929 | 1/2001 |
| JP | 2005-517486 A | 6/2005 |
| JP | 2005-529648 A | 10/2005 |
| WO | WO 96/06561 | 3/1996 |
| WO | WO 03/070101 A1 | 8/2003 |
| WO | WO 03/077763 A2 | 9/2003 |
| WO | WO 03/081220 A2 | 10/2003 |
| WO | WO 03/103496 A1 | 12/2003 |
| WO | WO 2004/017832 A2 | 3/2004 |
| WO | WO 2004/019279 A2 | 3/2004 |

OTHER PUBLICATIONS

Chabbal, J., et al., "Amorphous Silicon X-Ray Image Sensor", *Physics of Medical Imaging*, Proceedings of SPIE, Feb. 23-25, 1997, vol. 3032.

Hsiung, H., et al., "3D x-ray angiography: Study of factors affecting projection data consistency", *Physics of Medical Imaging*, Proceedings of SPIE, pp. 226-237, Feb. 23-25, 1997, vol. 3032.

Lwata, K., et al., "Description of a Prototype Combined CT-SPECT System with a Single CdZnTE Detector", *Nuclear Science Symposium Conference Record*, 2000 IEEE, XP010556613, pp. 16-1-16-5.

Lang, T.F., et al., "A Prototype Emission-Transmission Imaging System", *Proceedings of the Nuclear Science Symposium and Medical Imaging Conference*, 1991 IEEE, XP010058199, pp. 1902-1906.

Lang, Thomas, F., et al., "Description of a Prototype Emission—Transmission Computed Tomography Imaging System", *Journal of Nuclear Medicine, Society of Nuclear Medicine*, 1992, XP002901050, pp. 1881-1887.

Notification of Transmittal of the International Search Report for Int'l Application No. PCT/US02/40132, Date Mailed: Mar. 20, 2003.

Written Opinion for Int'l Application No. PCT/US02/40132, Date Mailed: Oct. 9, 2003.

Notification of Transmittal of the International Preliminary Examination Report for Int'l Application No. PCT/US02/40132, Date Mailed: Feb. 4, 2004.

Notification of Transmittal of the International Search Report for Int'l Application No. PCT/US03/08143, Date Mailed: Oct. 13, 2003.

Written Opinion for Int'l Application No. PCT/US03/08143, Date Mailed: Nov. 24, 2003.

Notification of Transmittal of the International Search Report for Int'l Application No. PCT/US03/08143, Date Mailed: Dec. 18, 2003.

Notification of Transmittal of the International Preliminary Examination Report for Int'l Application No. PCT/US03/08143, Date Mailed: Apr. 13, 2004.

Notification of Transmittal of the International Search Report for Int'l Application No. PCT/US03/08383, Date Mailed: Nov. 25, 2003.

Written Opinion for Int'l Application No. PCT/US03/08383, Date Mailed: Jan. 7, 2004.

Notification of Transmittal of the International Preliminary Examination Report for Int'l Application No. PCT/US03/08383, Date Mailed: Jun. 23, 2004.

Notification of Transmittal of the International Search Report for Int'l Application No. PCT/US03/18398, Date Mailed: Sep. 16, 2003.

Written Opinion for Int'l Application No. PCT/US03/18398, Date Mailed: Jun. 24, 2005.

Notification of Transmittal of the International Preliminary Examination Report for Int'l Application No. PCT/US03/18398, Date Mailed: Oct. 21, 2005.

Invitation to Pay Additional Fees and Partial International Search for Int'l Application No. PCT/US03/26120, Date Mailed: Feb. 13, 2004.

Notification of Transmittal of the International Search Report for Int'l Application No. PCT/US03/26120, Date Mailed: May 21, 2004.

Written Opinion for Int'l Application No. PCT/US03/26120, Date Mailed: Jul. 29, 2004.

Notification of Transmittal of the International Preliminary Examination Report for Int'l Application No. PCT/US03/26120, Date Mailed: Dec. 9, 2004.

Notification of Transmittal of the International Search Report for Int'l Application No. PCT/US03/26021, Date Mailed: Feb. 18, 2004.

Written Opinion for Int'l Application No. PCT/US03/26021, Date Mailed: Mar. 29, 2004.

Notification of Transmittal of the International Preliminary Examination Report for Int'l Application No. PCT/US03/26021, Date Mailed: Jul. 19, 2004.

\* cited by examiner

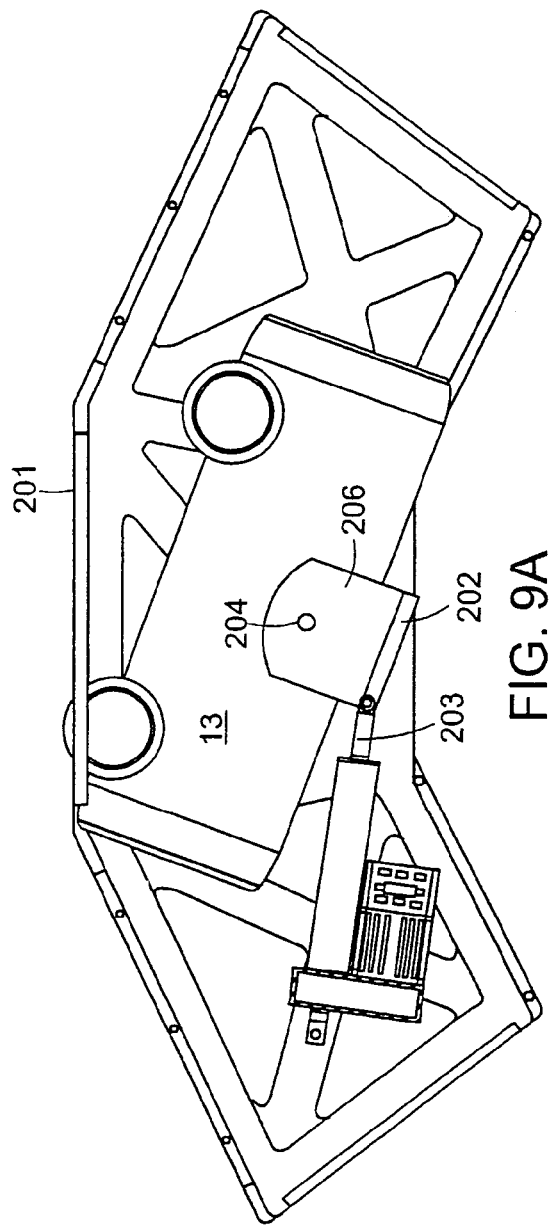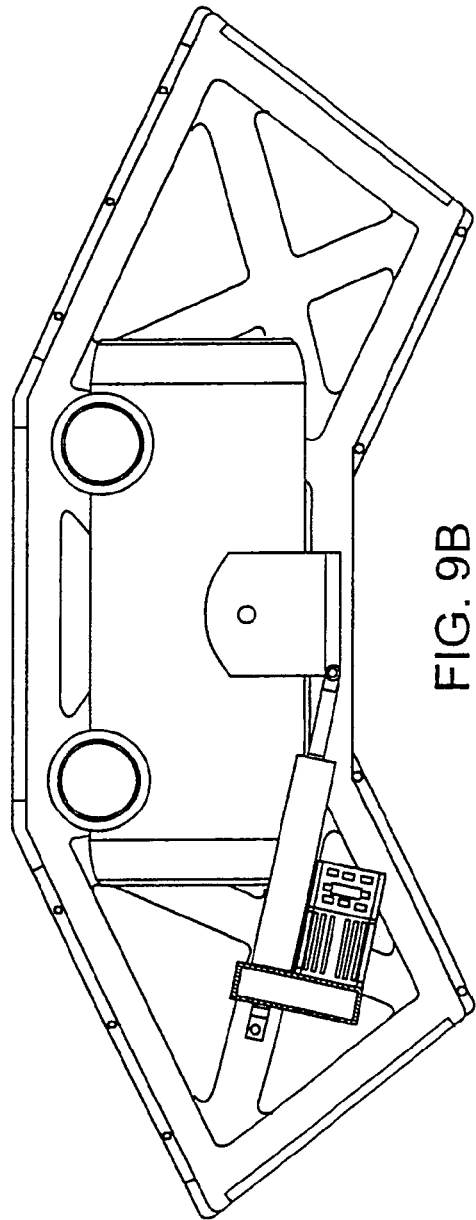

SYSTEMS AND METHODS FOR IMAGING LARGE FIELD-OF-VIEW OBJECTS

RELATED APPLICATION

This application is a continuation of U.S. application Ser. No. 10/392,365, filed Mar. 18, 2003, now U.S. Pat. No. 7,108,421 which claims the benefit of U.S. Provisional Application No. 60/366,062, filed Mar. 19, 2002. The entire teachings of the above applications are incorporated herein by reference.

BACKGROUND OF THE INVENTION

In conventional computerized tomography for both medical and industrial applications, an x-ray fan beam and a linear array detector are employed to achieve two-dimensional axial imaging. The quality of these two-dimensional (2D) images is high, although only a single slice of an object can be imaged at a time. To acquire a three-dimensional (3D) data set, a series of 2D images are sequentially obtained in what is known as the "stack of slices" technique. One drawback to this method is that acquiring the 3D data set one slice at a time is an inherently slow process. There are other problems with this conventional tomographic technique, such as motion artifacts arising from the fact that the slices cannot be imaged simultaneously, and excessive exposure to x-ray radiation due to overlap of the x-ray projection areas.

Another technique for 3D computerized tomography is cone-beam x-ray imaging. In a system employing cone-beam geometry, an x-ray source projects a cone-shaped beam of x-ray radiation through the target object and onto a 2D area detector area. The target object is scanned, preferably over a 360-degree range, either by moving the x-ray source and detector in a scanning circle around the stationary object, or by rotating the object while the source and detector remain stationary. In either case, it is the relative movement between the source and object which accomplishes the scanning. Compared to the 2D "stack of slices" approach for 3D imaging, the cone-beam geometry is able to achieve 3D images in a much shorter time, while minimizing exposure to radiation. One example of a cone beam x-ray system for acquiring 3D volumetric image data using a flat panel image receptor is discussed in U.S. Pat. No. 6,041,097 to Roos, et al.

A significant limitation of existing cone-beam reconstruction techniques occurs, however, when the object being imaged is larger than the field-of-view of the detector, which is a quite common situation in both industrial and medical imaging applications. In this situation, some measured projections contain information from both the field of view of interest and from other regions of the object outside the field of view. The resulting image of the field of view of interest is therefore corrupted by data resulting from overlying material.

Several approaches have been proposed for imaging objects larger than the field-of-view of the imaging system. U.S. Pat. No. 5,032,990 to Eberhard et al., for example, discusses a technique for 2D imaging of an object which is so wide that a linear array detector is not wide enough to span the object or part which is to be viewed. The method involves successively scanning the object and acquiring partial data sets at a plurality of relative positions of the object, x-ray source, and detector array. U.S. Pat. No. 5,187,659 to Eberhard et al. discusses a technique for avoiding corrupted data when performing 3D CT on an object larger than the field of view. This technique involves scanning the object with multiple scanning trajectories, using one or more x-ray sources and detectors which rotate in different trajectories relative to the target object. Yet another technique is discussed in U.S. Pat. No. 5,319,693 to Ebarhard et al. This patent discusses simulating a relatively large area detector using a relatively small area detector by either moving the actual area detector relative to the source, or moving the object relative to the area detector. All of these techniques are characterized by complex relative movements between one or more x-ray sources, detectors, and the object being imaged. Furthermore, in each of these techniques, the target object is exposed to excessive x-ray radiation from regions of overlapping projections.

To date, there does not exist a radiation system for imaging large field-of-view objects in a simple and straightforward manner while minimizing the target object's exposure to radiation.

SUMMARY OF THE INVENTION

The present invention relates to radiation-based imaging, including 3D computerized tomography (CT) and 2D planar x-ray imaging. In particular this invention relates to methods and systems for minimizing the amount of missing data and, at the same time, avoiding corrupted and resulting artifacts in image reconstruction when a cone-beam configuration is used to image a portion of an object that is larger than the field of view.

An imaging apparatus according to one aspect comprises a source that projects a beam of radiation in a first trajectory; a detector located a distance from the source and positioned to receive the beam of radiation in the first trajectory; an imaging area between the source and the detector, the radiation beam from the source passing through a portion of the imaging area before it is received at the detector; a detector positioner that translates the detector to a second position in a first direction that is substantially normal to the first trajectory; and a beam positioner that alters the trajectory of the radiation beam to direct the beam onto the detector located at the second position. The radiation source can be an x-ray cone-beam source, and the detector can be a two-dimensional flat-panel detector array.

By translating a detector of limited size along a line or arc opposite the radiation source, and obtaining object images at multiple positions along the translation path, an effectively large field-of-view may be achieved. In one embodiment, a detector positioner for translating the detector comprises a positioner frame that supports the detector and defines a translation path, and a motor that drives the detector as it translates within the positioner frame. A positioning feedback system, which can include a linear encoder tape and a read head, can be used to precisely locate and position the detector within the positioner frame. Other position encoder systems could also be used as the positioning feedback system, such as a rotary encoder and a friction wheel.

A radiation source, such as an x-ray source, includes a beam positioning mechanism for changing the trajectory of the emitted radiation beam from a fixed focal spot. This enables the beam to scan across an imaging region, and follow the path of a moving target, such as a translating detector array. In one aspect, the beam positioning mechanism of the present invention enables safer and more efficient dose utilization, as the beam positioner permits the beam to sequentially scan through limited regions of the target object, so that only the region within the field-of-view of the translating detector at any given time need be exposed to harmful radiation.

In one embodiment, a tilting beam positioning mechanism includes a frame which houses the radiation source, and a motorized system connected to both the frame and the source, where the motorized system pivots or tilts the source relative to the frame to alter the trajectory of the radiation beam projected from the source. In a preferred embodiment, the source is pivoted about the focal spot of the projected radiation beam. The motorized tilting system could include, for example, a linear actuator connected at one end to the fixed frame and at the other end to the source, where the length of the actuator controls the angle of tilt of the source, or a motorized pulley system for tilting the source. In another embodiment, a movable collimator is driven by a motor for changing the trajectory of the output beam.

In still another aspect, the invention includes means for rotating the source and translatable detector relative to an object to obtain images at different projection angles over a partial or full 360-degree scan. In one embodiment, the source and detector are housed in a gantry, such as a substantially O-shaped gantry ring, and are rotatable around the inside of the gantry ring. The source and detector can be mounted to a motorized rotor which rotates around the gantry on a rail and bearing system. In another embodiment, the source and translatable detector remain fixed on a support, such as a table, while the object rotates on a turntable or rotatable stage.

The invention also relates to a method of imaging an object comprising projecting a beam of radiation in a first trajectory, the beam traveling through a first region of the object and onto a detector located at a first position; translating the detector to a second position in a direction that is substantially normal to the first trajectory; and altering the trajectory of the beam so that the beam travels through a second region of the object and onto the detector located at the second position. Preferably, the beam of radiation comprises a cone-beam or fan-beam of x-ray radiation, and the detected radiation is used to produce two-dimensional planar or three-dimensional computerized tomographic (CT) object images.

In one aspect, the invention is able to image objects larger than the field-of-view of the detector in a simple and straightforward manner by utilizing a detector positioner that translates the detector array to multiple positions, thus providing an effectively large field-of-view using only a single detector array having a relatively small size. In addition, a beam positioner permits the trajectory of the beam to follow the path of the translating detector, which advantageously enables safer and more efficient dose utilization, as only the region of the target object that is within the field-of-view of the detector at any given time needs to be exposed to harmful radiation.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 9A-C shows an x-ray source tilted to three positions by a linear actuator, according to one embodiment of the invention;

DETAILED DESCRIPTION OF THE INVENTION

A description of preferred embodiments of the invention follows.

Figure 1:
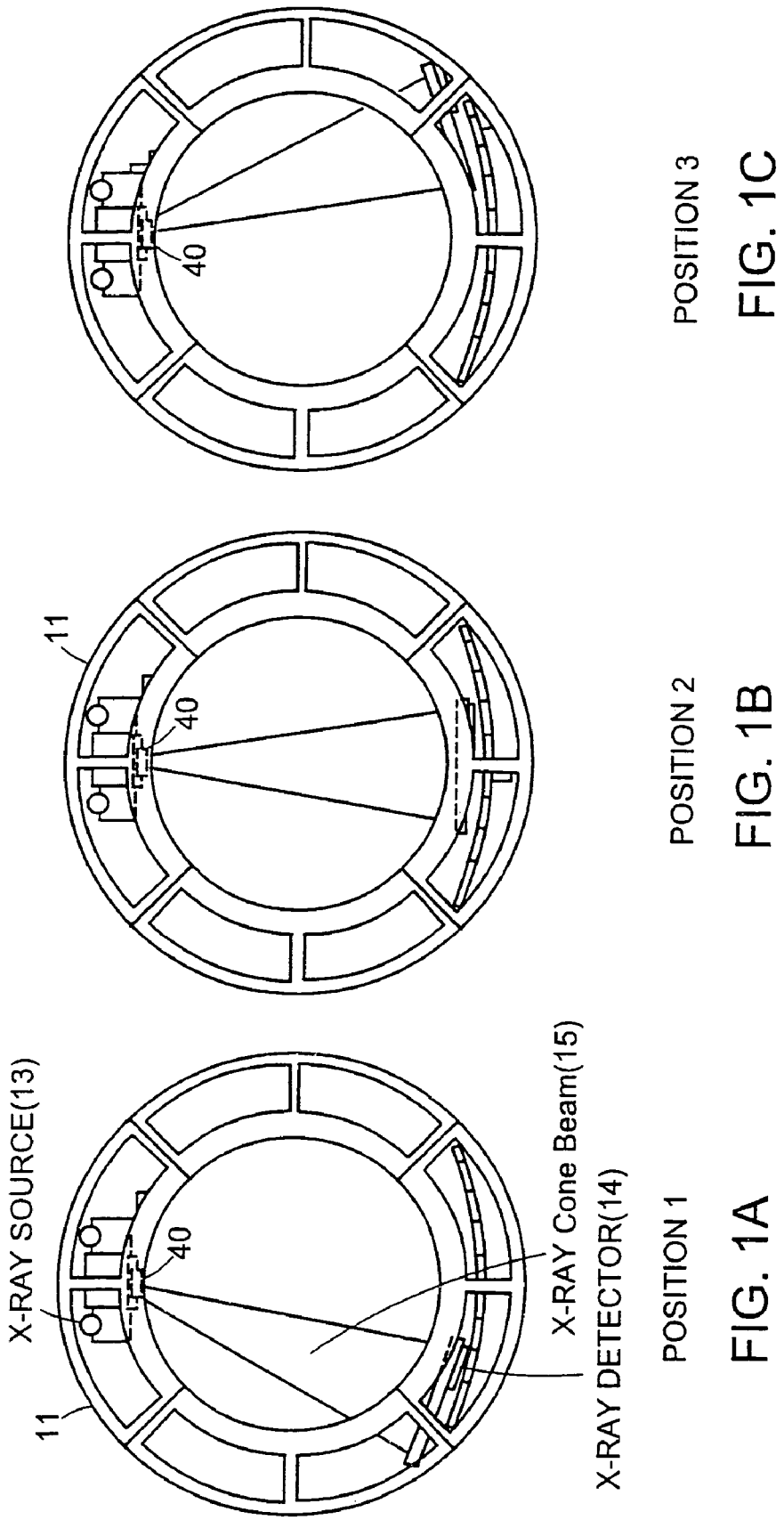
FIGS. 1A-C are schematic diagrams showing an x-ray scanning system with a translating detector array according to one embodiment of the invention.

FIGS. 1A-C schematically illustrate an x-ray scanning system with a translating detector array according to one embodiment of the invention. The scanning system shown in FIGS. 1A-C includes gantry 11, which in this embodiment comprises a generally circular, or "O-shaped," housing having a central opening into which an object being imaged is placed. The gantry 11 contains an x-ray source 13 (such as a rotating anode pulsed x-ray source) that projects a beam of x-ray radiation 15 into the central opening of the gantry, through the object being imaged, and onto a detector array 14 (such as a flat panel digital detector array) located on the opposite side of the gantry. The x-rays received at the detector 14 can then be used to produce a 2D planar or 3D tomographic object reconstruction images using well-known techniques.

Figure 2:
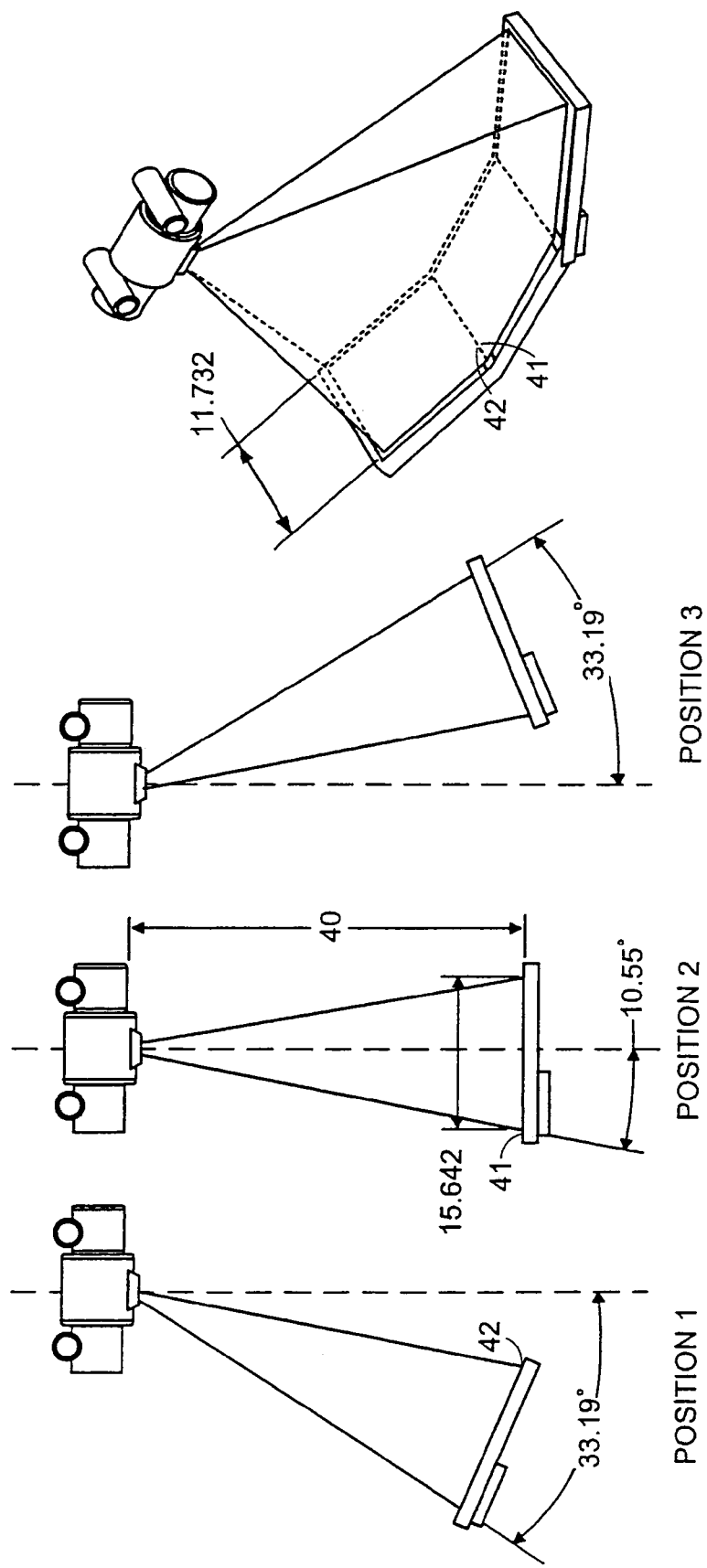
FIGS. 2A-D are side and perspective views illustrating the x-ray source and detector of the system of FIG. 1.
Figure 16:
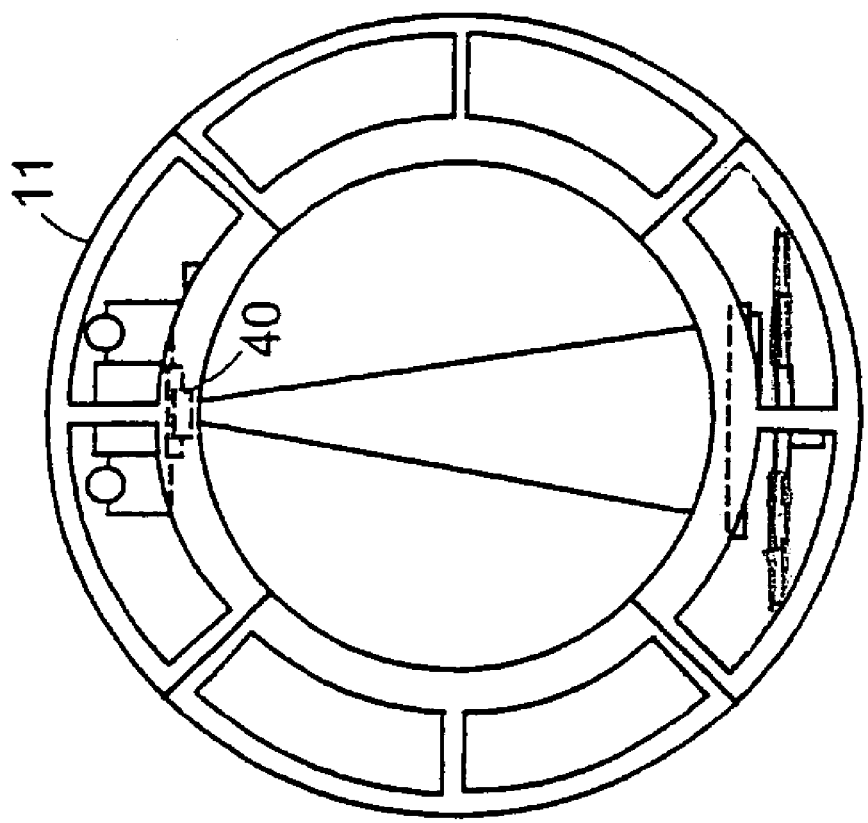
FIG. 16 shows a detector that is translated along a line.

The detector 14 is translated to multiple positions along a line or arc in a direction that is generally normal to the trajectory of beam 15. This permits the detector to capture images of objects that are wider than the field-of-view of the detector array. FIGS. 1A-1C show the large field-of-view imaging area when the detector is translated to three positions along an arc opposite the x-ray source. This is more clearly illustrated in FIGS. 2A-C, which are side views of the source and detector as the detector translates to three different positions. FIG. 2D is a perspective view showing the resultant large imaging field-of-view by combining the data obtained at all three source and detector positions. As shown in FIGS. 2A-C, as the detector moves to each subsequent position, the last column of detector pixels 41 is positioned adjacent to the location of the leading column of pixels 42 from the prior detector position, thereby providing a large "effective" detector having a wide field-of-view, as shown in FIG. 2D. The image obtained is a combination of the three images abutted against one another, resulting in a large field-of-view using only a single detector array having a relatively small size. The detector 14 being translated along a line is illustrated in FIG. 16.

The source 13 preferably includes a beam positioning mechanism for changing the trajectory of the beam 15 from a stationary focal spot 40, so that the beam follows the detector as the detector translates, as shown in FIGS. 1A-C. This permits safer and more efficient dose utilization, as generally only the region of the target object that is within the field-of-view of the detector at any given time will be exposed to potentially harmful radiation.

Preferably, the translational movement of the detector and the trajectory of the x-ray beam can be automatically coordinated and controlled by a computerized motor control system.

Figure 3:
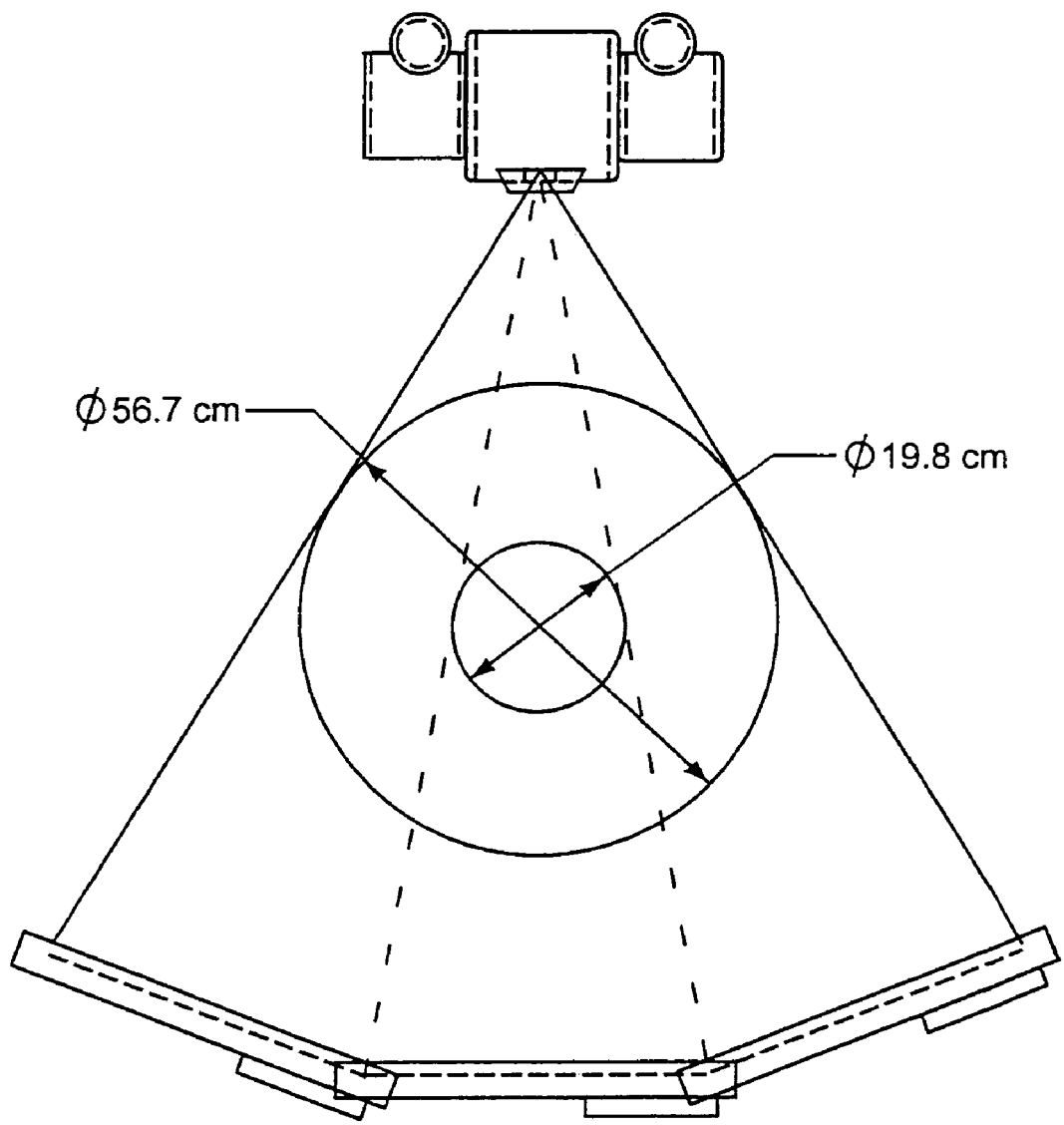
FIG. 3 illustrates the wide field-of-view achievable with the translating detector system of the present invention.

FIG. 3 illustrates the large field-of-view obtainable using the translating detector array of the present invention, as compared to the field-of-view of the same array in a conventional static configuration. The small and large circles represent varying diameters of the region centered on the axis of the imaging area that is within the field-of-view of the detector for the non-translatable and translatable arrays, respectively. The diameter of this imaging region is approximately half the width of the detector, since the beam diverges in the shape of a cone as it projects from the focal spot of the source onto the detector array. As shown in FIG. 3, the diameter of this imaging region can be greatly increased by translating the detector array and scanning the x-ray beam to multiple positions along a line or arc on the gantry.

In one aspect, the x-ray source 13 and translatable detector 14 are rotatable around the interior of the gantry, preferably on a motorized rotor, to obtain large field-of-view x-ray images from multiple projection angles over a partial or full 360-degree rotation. Collection of multiple projections throughout a full 360-degree rotation results in sufficient data for three-dimensional cone-beam tomographic reconstruction of the target object.

Figure 4:
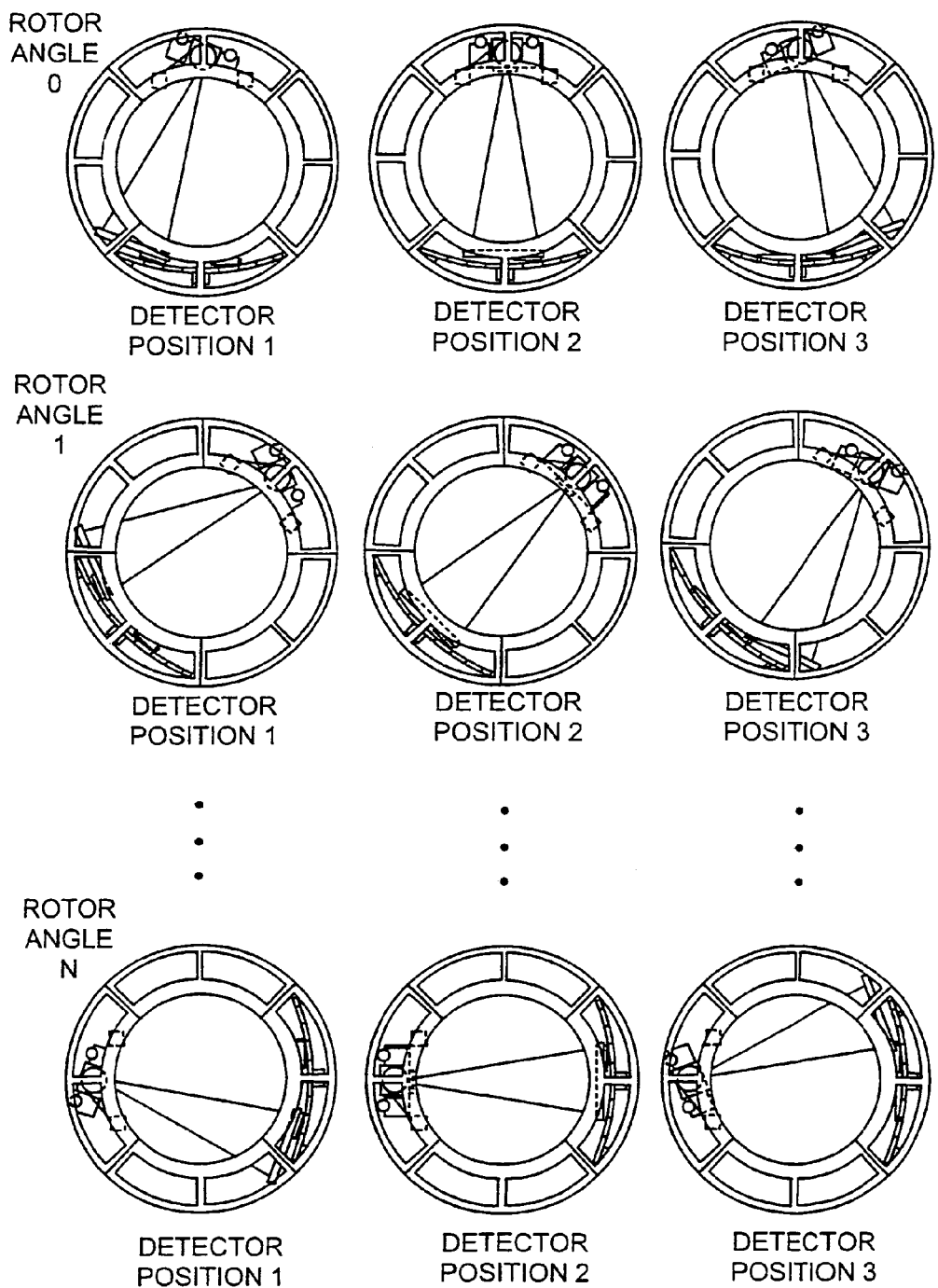
FIG. 4 is a schematic diagram showing a data collection matrix of an x-ray scanner system according to one embodiment of the invention.

As shown in the matrix diagram of FIG. 4, there are at least two methods for obtaining large field-of-view images over a partial or full 360-degree rotational scan of the target object. In the first method, for each rotational angle of the source and detector within the gantry, the detector is translated to two or more positions, capturing x-ray images at each detector position. This is shown in the top row of the matrix diagram of FIG. 4, where the x-ray source and detector stage are maintained at Rotor Angle 0, while the detector translates on the stage to Detector Positions 1-3. The rotor carrying the x-ray source and detector stage then rotate to a second position on the gantry, Rotor Angle 1, and the detector again translates to the three detector positions. This process repeats as the x-ray source and detector stage rotate through N rotor positions on the gantry to obtain large field-of-view object images over a full 360-degree scan.

In a second method, for each position of the translating detector, the source and detector stage perform a partial of full 360-degree rotation around the target object. This is shown in the leftmost column of the matrix diagram of FIG. 4, where detector is maintained at Detector Position 1, while the source and detector stage rotate within the gantry to Rotor Angles 0 through N. Then, as shown in the center column of FIG. 4, the detector is translated to Detector Position 2, and the source and detector stage are again rotated to Rotor Angles 0 through N. This process is repeated for each position of the translating detector array, with the source and detector stage performing a partial or full scan around the target object for each detector position.

Figure 5:
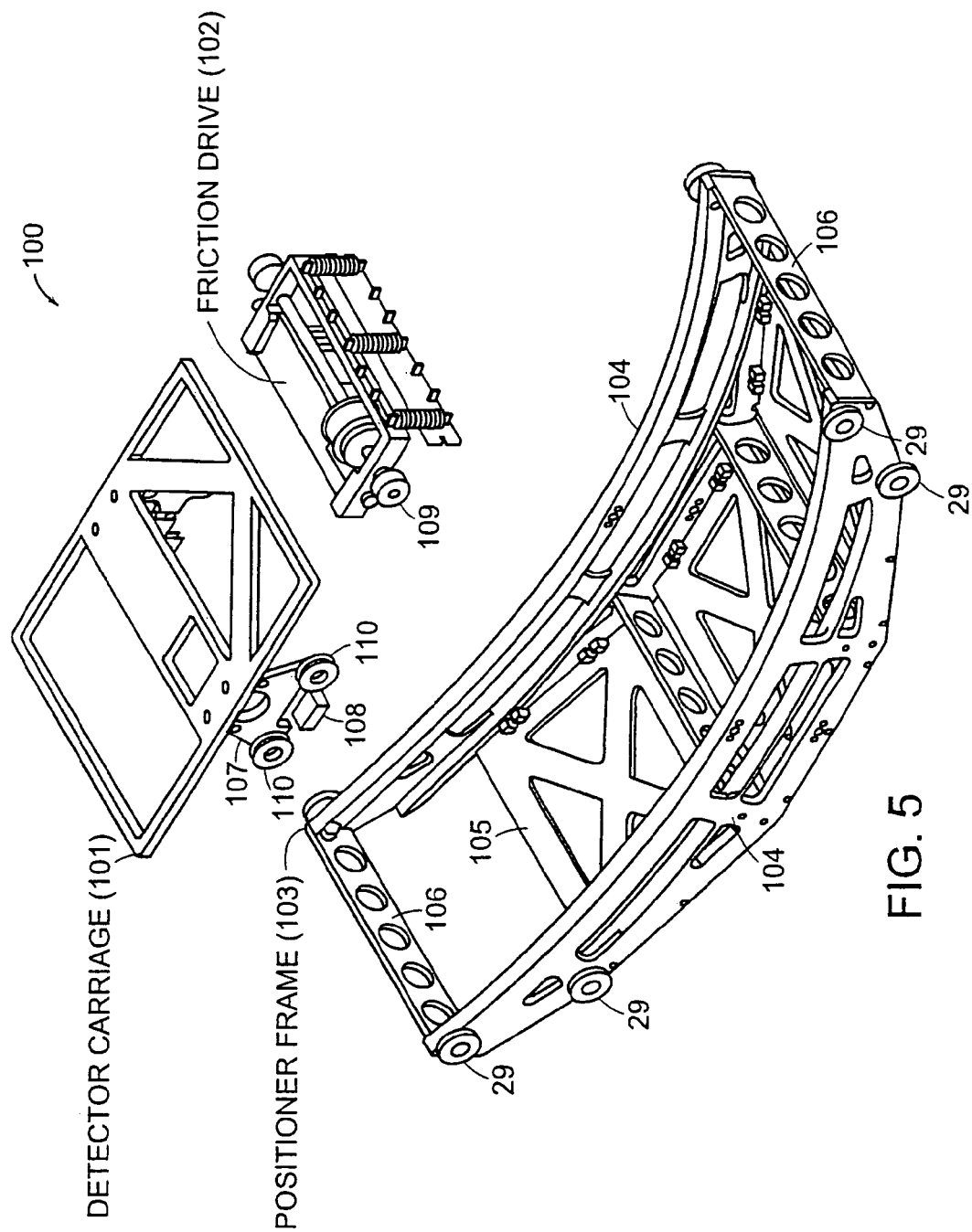
FIG. 5 is an exploded view of an x-ray detector positioning stage according to one embodiment.

Turning now to FIG. 5, an x-ray detector positioner 100 according to one embodiment of the invention is shown in exploded form. The positioning stage comprises a detector carriage 101 for holding the detector, a friction drive 102 which attaches to the detector carriage, and a positioner frame 103 upon which the detector carriage is movably mounted. The positioner frame includes two parallel side walls 104, a base 105, and a series of lateral frames 106 extending between the side walls. The interior of the side walls 104 include three main concentric surfaces extending the length of the frame. On top of each side wall 104 is a flat surface upon which a friction wheel 109 is driven, in the center is a v-groove rail on which a pair of v-groove rollers 110 ride, and on the bottom is another flat surface upon which a linear encoder tape is affixed.

In the embodiment shown, the concentric radii of the components of the curved side rails vary as a function of a circumscribed circle centered at the focal spot of an x-ray source. The central ray or line that connects the focal spot to the center pixel of the detector array is essentially perpendicular to the flat face of the detector array. By moving the translating detector components along the defined curved side rails, the face of the detector translates tangentially to the circle circumscribed by connecting the ray or line that connects the focal spot to the center pixel of the detector array. Other embodiments include a circle with infinite radius, in which case the curved side rails become straightened along a flat plane or line.

The friction drive 102 consists of a servomotor, gear head, belt drive, axle, and friction wheels 109. The friction drive is mounted to the detector carriage 101 by brackets 107. The friction wheels 109 are preferably spring-loaded and biased against the flat top surface of the side walls 104. The rollers 110 are mounted to brackets 107, and pressed into the central v-grooves of the positioner side walls 104. The v-groove rollers 110 precisely locate the detector carriage 101 as well as allow loading from any direction, thus enabling the accurate positioning of the translated detector array independent of gantry angle or position. The friction wheel 109 minimizes the backlash in the positioning system. In addition, a read head 108 is located on a detector carriage bracket 107 for reading the encoder tape affixed to the bottom flat surface of the positioner side wall 104. The read head 108 provides position feedback information to the servomotor for precise positioning of the detector carriage along the concentric axis of travel. The x-ray detector positioner 100 can also include bearings 29 attached to side walls 104 for rotating the entire detector assembly around the interior of a gantry, as described in further detail below.

Figure 6A:
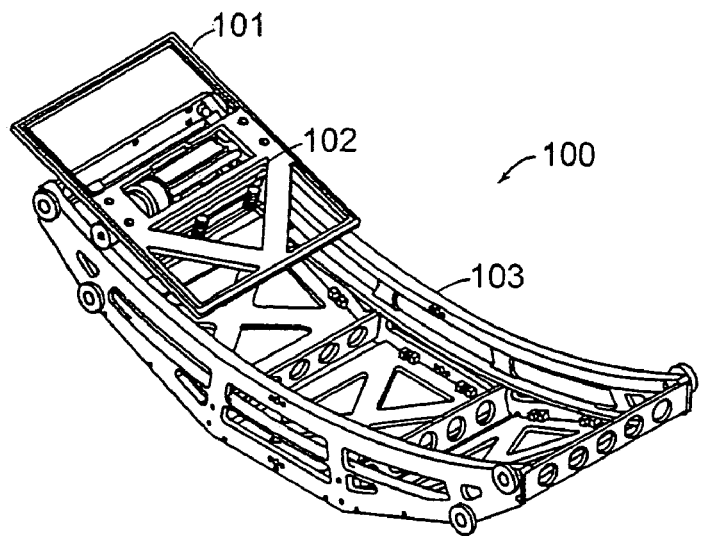
FIGS. 6A-C shows the x-ray detector positioning stage translating to three positions.
Figure 6B:
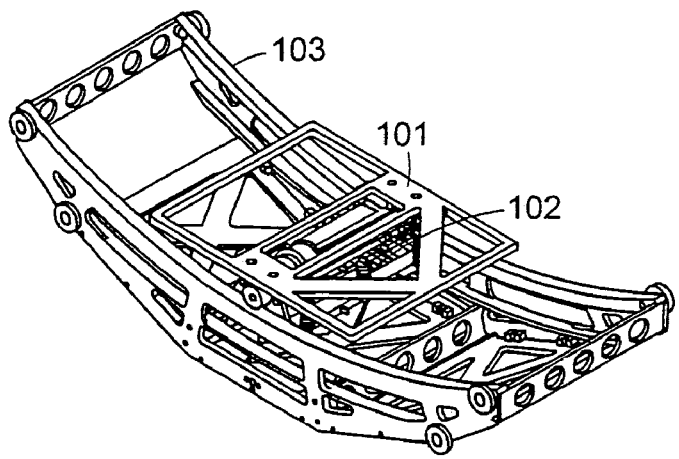
Figure 6C:
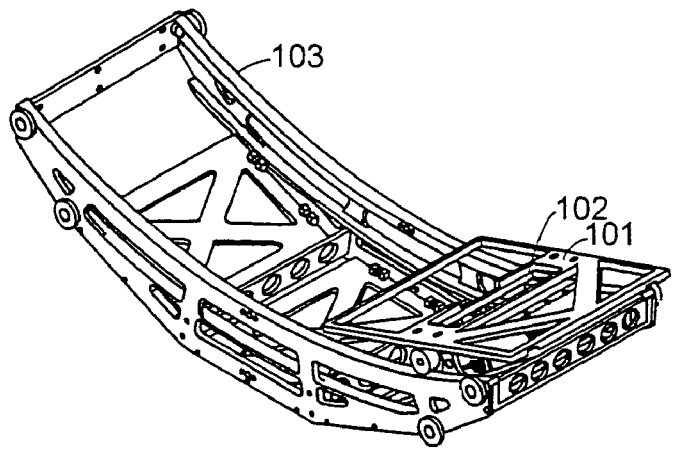

Referring to FIGS. 6A-C, the assembled detector positioner 100 is shown translating the detector carriage 101 to multiple positions along an arc. In operation, the detector carriage 101 and friction drive assembly 102 are precisely moved by the servomotor along the concentric axis of the positioning frame and accurately positioned by the linear encoder system. Three positions are shown in FIGS. 6A-C, although the detector carriage 101 may be precisely positioned at any point along the arc defined by the positioner frame 103. The compact nature of the friction drive 102 allows for maximum translation of the detector carriage 101 while the drive 102 remains completely enclosed within the positioner frame 103, and allows the distal ends of the detector carriage to extend beyond the edge of the positioner frame (as shown in FIGS. 6A and 6C) to further increase the "effective" field-of-view obtainable with the detector.

Figure 7:
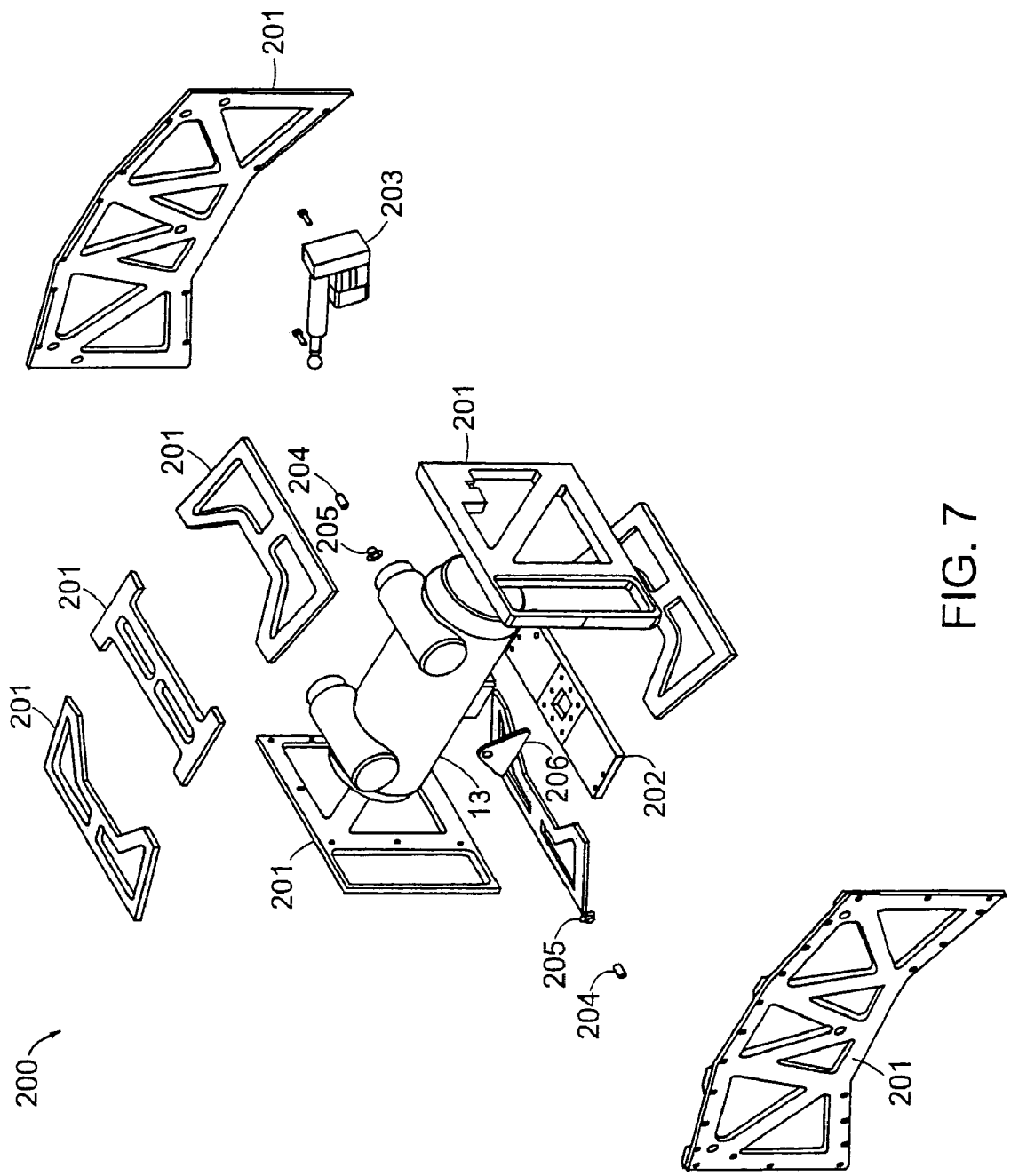
FIG. 7 is an exploded view of an x-ray source and source positioning stage according to one embodiment of the invention.

As discussed above, the imaging system of the present invention preferably includes a radiation source with a beam positioning mechanism for changing the trajectory of the radiation emitted from a fixed focal spot, so that the beam may scan across multiple positions. One embodiment of an x-ray source stage 200 with a beam positioning mechanism is shown in FIG. 7. The stage comprises an outer wall frame 201 (shown in exploded form) which encloses the x-ray source 13, a swiveling x-ray source mount 202, and a servomotor linear actuator 203. The x-ray source is supported on the bottom by source mount 202 and from the sides by a pair of bushing mounts 206. The bushing mounts 206 are connected to the outer wall frame 201 by precision dowel pins 204 that are press-fit into bushings 205. The dowel pins 204 permit the bushing mounts 206, and thus the x-ray source 13 and source mount 202, to pivot with respect to the outer wall frame 201 pivoting motion. This pivoting motion is preferably centered at the focal spot of the x-ray source.

Figure 8:
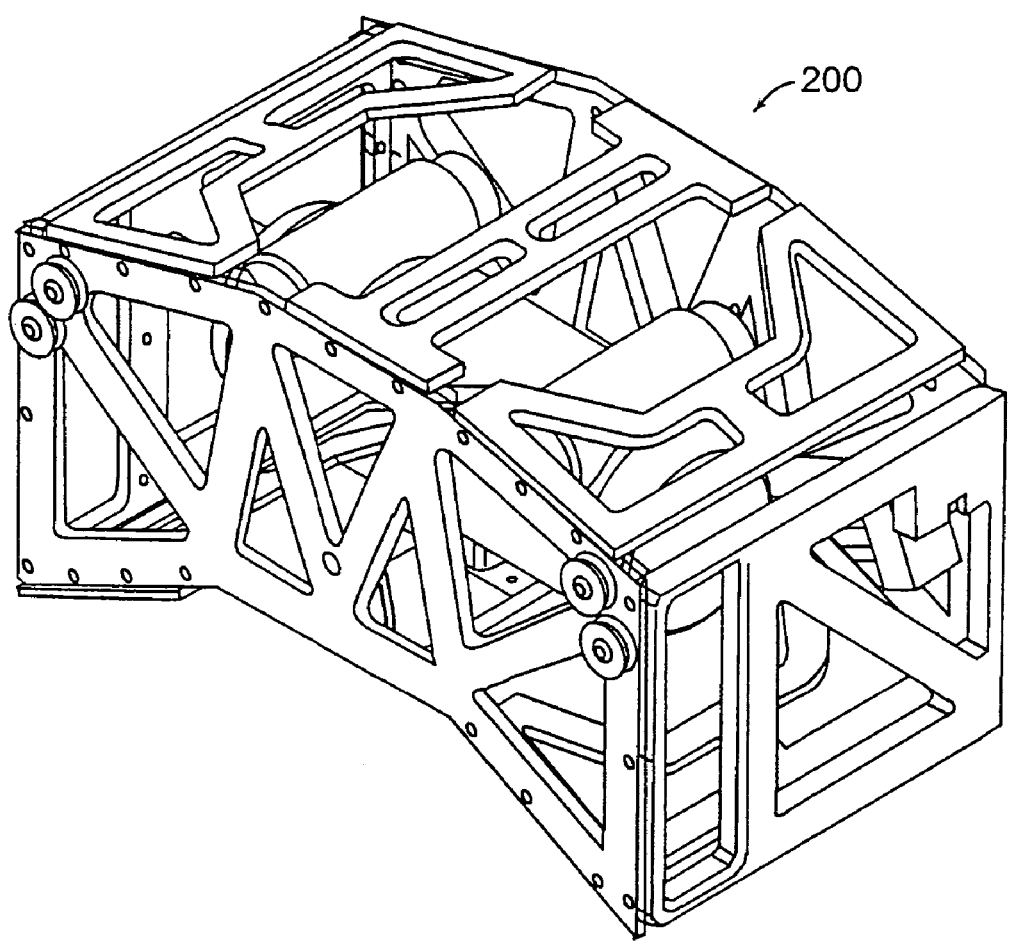
FIG. 8 is a perspective view of an assembled x-ray source and positioning stage.

The precision servomotor linear actuator 203 is attached at one end to the outer wall frame 201, and at the other end to the swiveling x-ray source mount 202. By varying the length of the motorized linear actuator 203, the source mount 202 and x-ray source 13 can be pivoted about dowel pins 204 to tilt the x-ray source about its focal spot in a controlled manner. The fully assembled x-ray source stage is shown in FIG. 8.

Figure 9C:
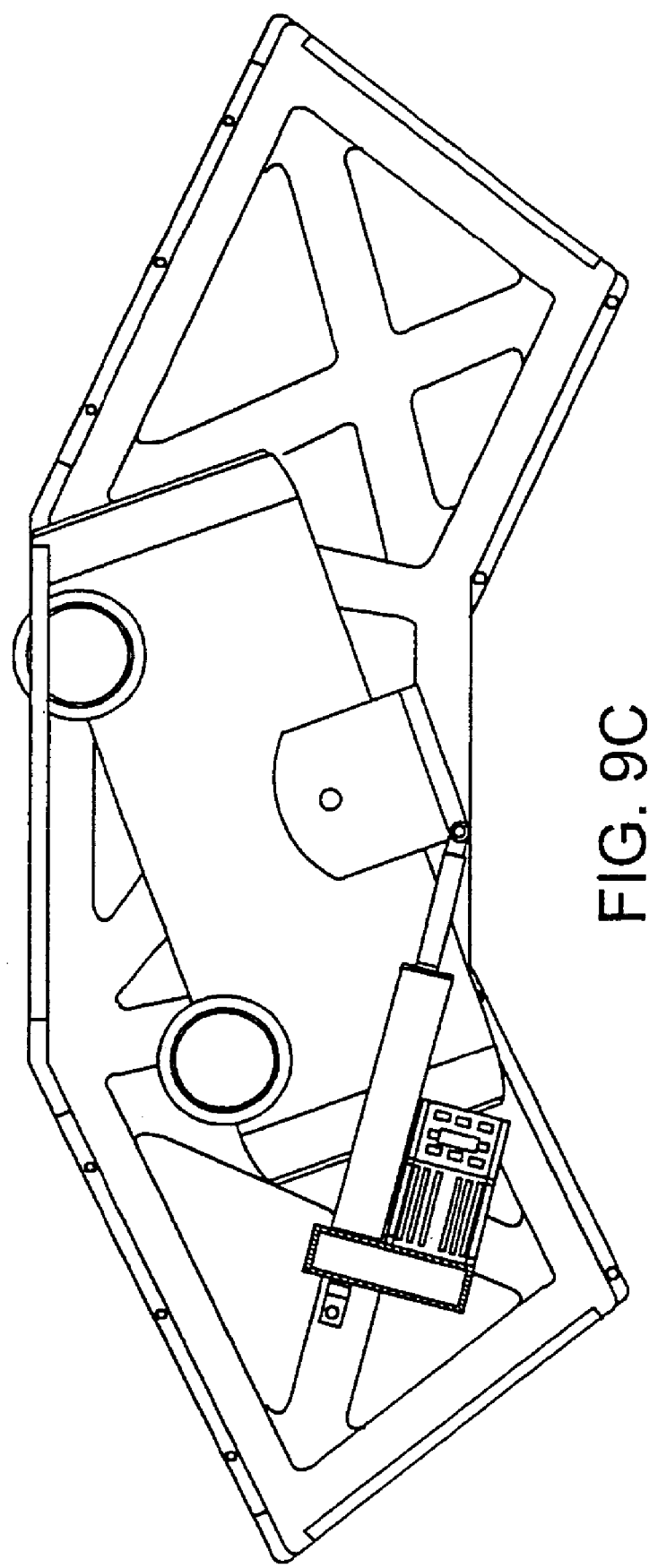

The operation of the x-ray source and tilting beam positioning mechanism is shown in FIGS. 9A-9C. As the linear actuator moves from a fully retracted position (FIG. 9A) to a fully extended position (FIG. 9C) the x-ray source pivots about its focal spot, thus altering the trajectory of the emitted radiation beam. In this embodiment, the pivot point represents the center of a circle with a radius defined by the distance from the focal spot to the center pixel of the detector array. The pivot angle is computed by determining the angle defined by the line connecting the focal spot of the x-ray detector and the center pixel of the detector array. A computerized motion control system can be used to synchronize the x-ray source tilt angle with the position of a translating detector array so that the x-ray beam remains centered on the detector even as the detector translates to different positions.

Figure 10:
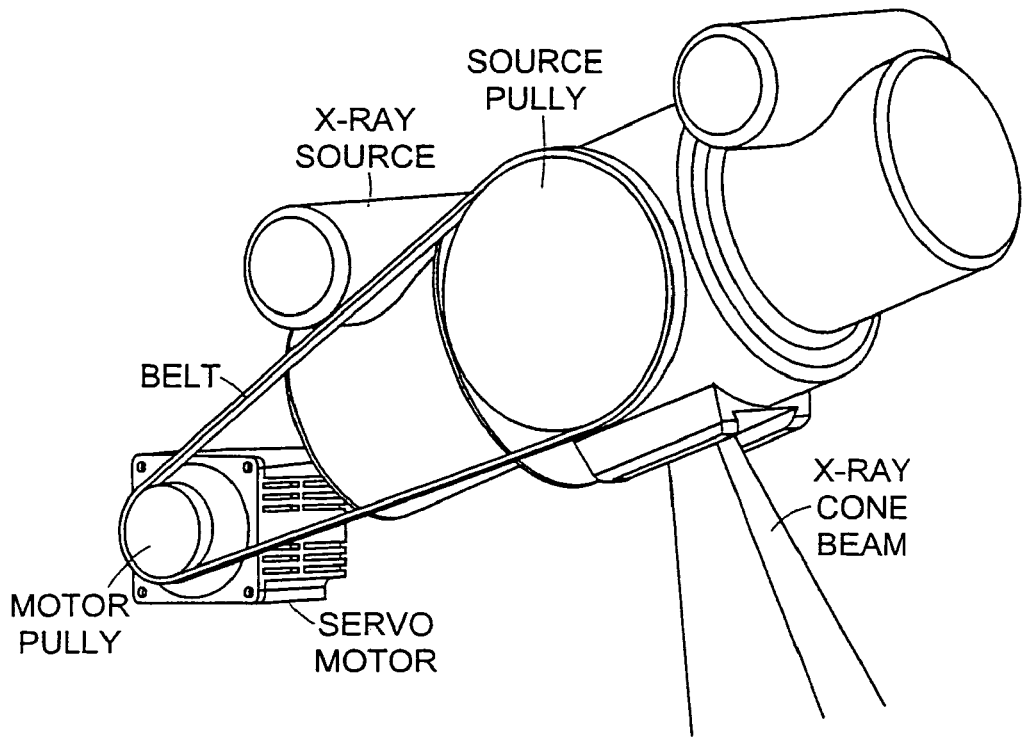
FIG. 10 shows a motorized belt and pulley system for tilting an x-ray source to multiple positions, according to another embodiment.
Figure 11:
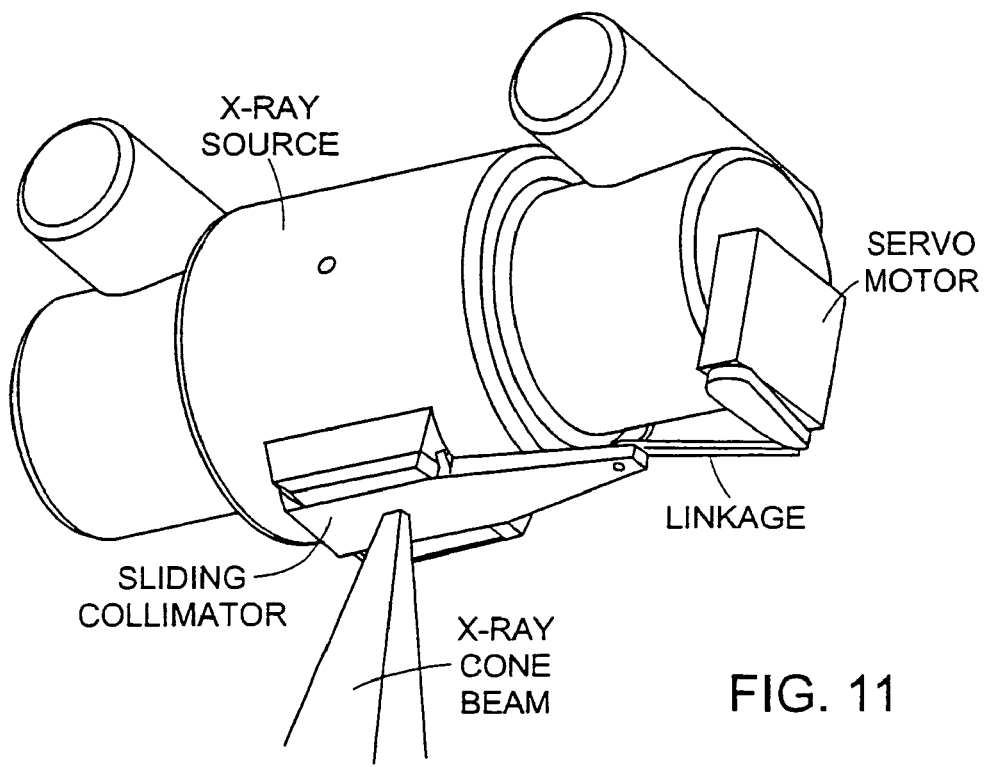
FIG. 11 shows a motorized sliding collimator for directing an x-ray beam to multiple detector positions, according to yet another embodiment.

Various other embodiments of an x-ray beam positioner can be employed according to the invention. For example, as shown in FIG. 10, the x-ray source can be tilted to multiple positions by a motorized belt and pulley system. In another embodiment shown in FIG. 11, the trajectory of the x-ray beam is altered by a sliding collimator that is driven by a servomotor.

Figure 12:
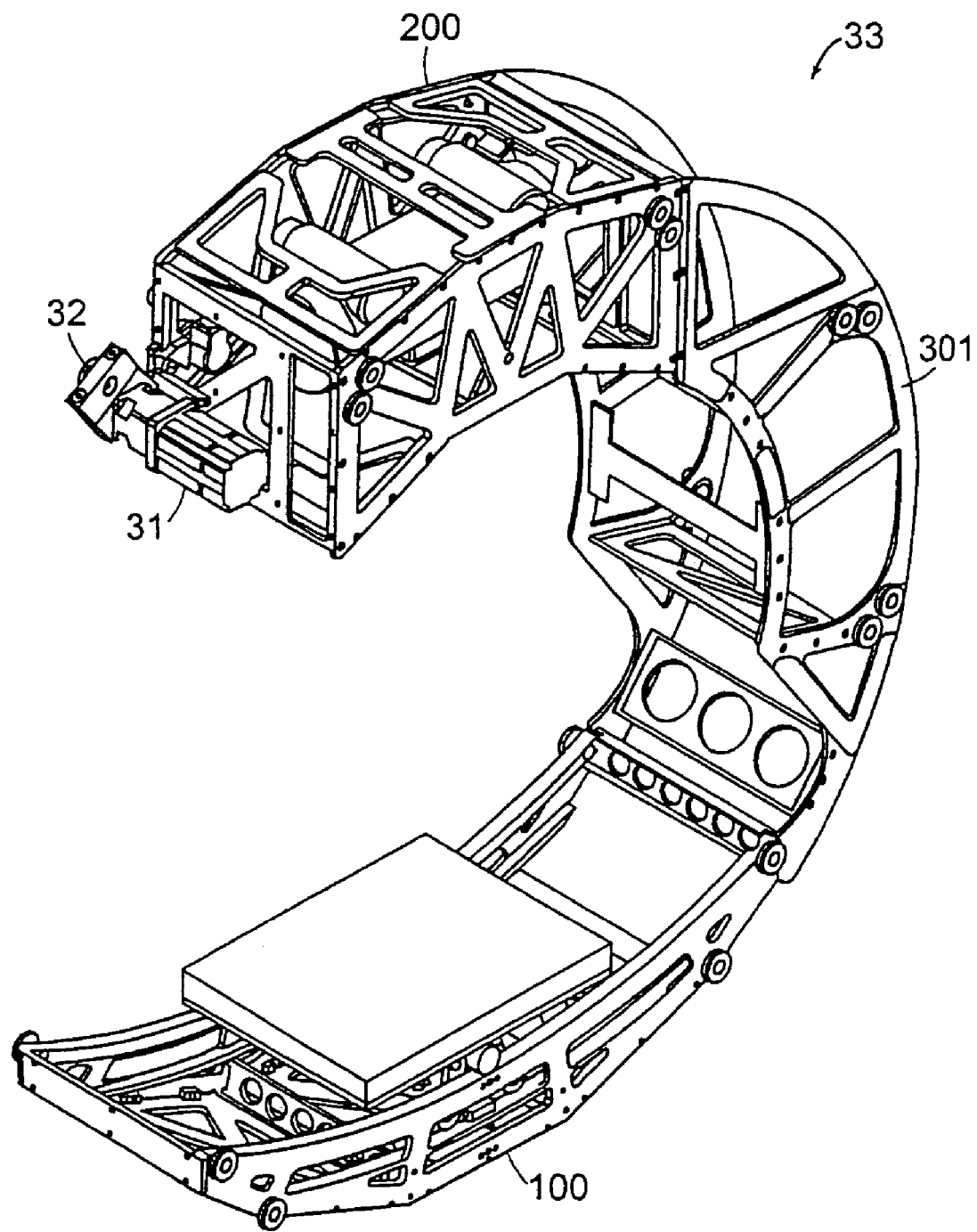
FIG. 12 is a perspective view of a rotor assembly for rotating an x-ray source and detector within a gantry.

As shown in FIG. 12, the x-ray source stage 200 and x-ray detector positioner 100 can be joined together by a curved bracket assembly 301 to produce a C-shaped motorized rotor assembly 33. The rigid bracket 301 maintains the source and detector opposed to one another, and the entire rotor assembly can be rotated inside an O-shaped x-ray gantry. The rotor assembly 33 can also include a motor 31 and drive wheel 32 attached at one end of the rotor for driving the rotor assembly around the interior of the gantry.

Figure 13:
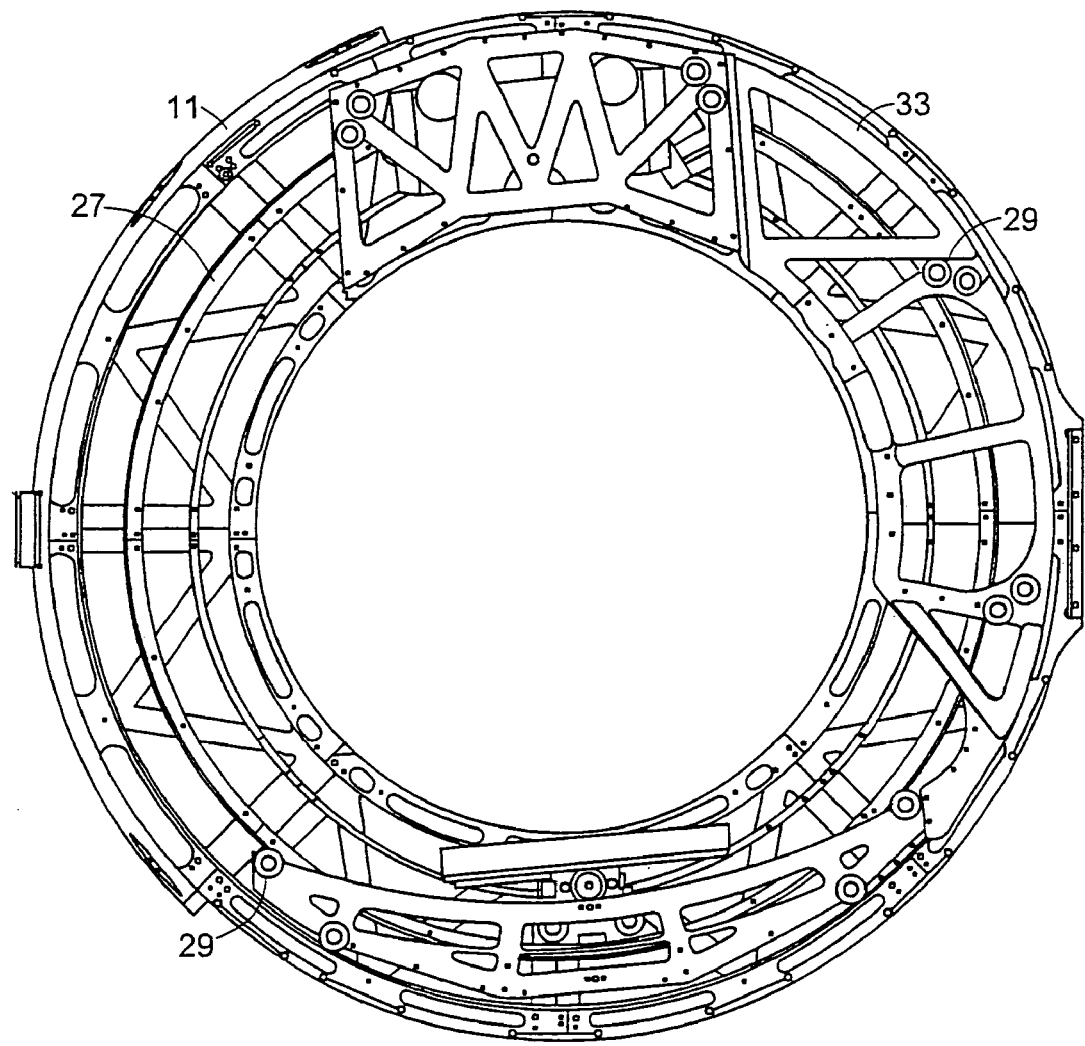
FIG. 13 is a cutaway side view showing the rotor assembly within a gantry ring.

FIG. 13 is a cutaway side view of a gantry 11 which contains a C-shaped motorized rotor 33. The interior side walls of the gantry include curved rails 27 extending in a continuous loop around the interior of the gantry. The drive wheel 32 of the rotor assembly 33 contacts the curved rail 27 of the gantry, and uses the rail to drive the rotor assembly around the interior of the gantry. A rotary incremental encoder can be used to precisely measure the angular position of the rotor assembly within the gantry. The incremental encoder can be driven by a friction wheel that rolls on a concentric rail located within the sidewall of the gantry. The rotor assembly 33 also includes bearings 29, which mate with the curved rails 27 of the gantry to help guide the rotor assembly 33 as it rotates inside the gantry. The interior of the gantry ring 11 can include a slip ring that maintains electrical contact with the rotor assembly 33 to provide the power needed to operate the x-ray source, detector, detector positioner, and/or beam positioner, and also to rotate the entire assembly within the gantry frame. The slip ring can furthermore be used to transmit control signals to the rotor, and x-ray imaging data from the detector to a separate processing unit located outside the gantry. Any or all of the functions of the slip ring could be performed by other means, such as a flexible cable harness attached to the rotor, for example.

Although the rotor assembly of the preferred embodiment is a C-shaped rotor, it will be understood that other rotor configurations, such as O-shaped rotors, could also be employed. For example, a second curved bracket 301 could be attached to close the open end of the rotor, and provide a generally O-shaped rotor. In addition, the x-ray source and detector could rotate independently of one another using separate mechanized systems.

Figure 14:
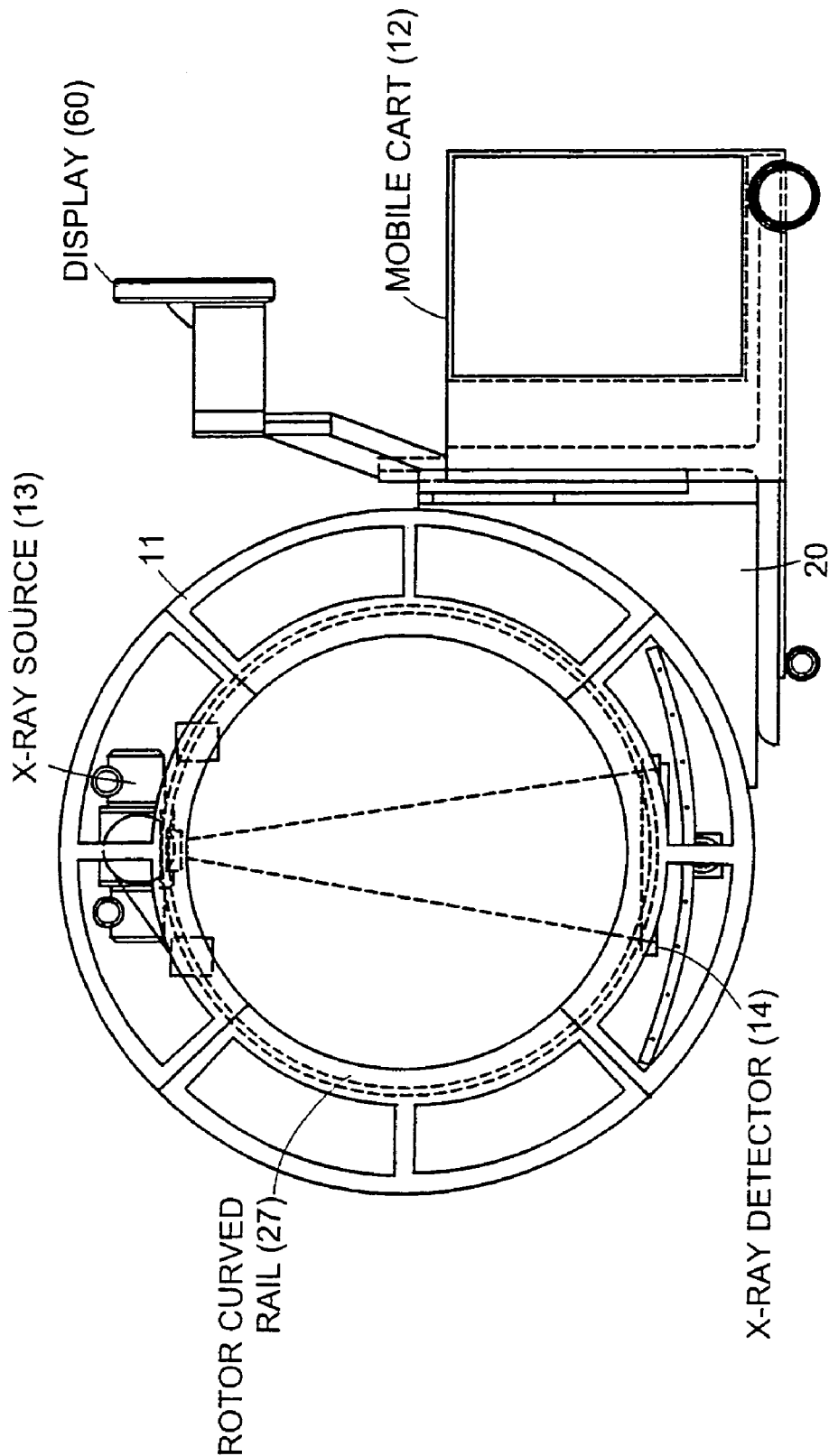
FIG. 14 is a schematic illustration of a mobile cart and gantry assembly for tomographic and planar imaging of large field-of-view objects according to one embodiment.

An x-ray scanning system 10 according to one aspect of the invention generally includes a gantry 11 secured to a support structure, which could be a mobile or stationary cart, a patient table, a wall, a floor, or a ceiling. As shown in FIG. 14, the gantry 11 is secured to a mobile cart 12 in a cantilevered fashion via a ring positioning unit 20. In certain embodiments, the ring positioning unit 20 enables the gantry 11 to translate and/or rotate with respect to the support structure, including, for example, translational movement along at least one of the x-, y-, and z-axes, and/or rotation around at least one of the x- and y-axes. X-ray scanning devices with a cantilevered, multiple-degree-of-freedom movable gantry are described in commonly owned U.S. Provisional Application 60/388,063, filed Jun. 11, 2002, and 60/405,098, filed Aug. 21, 2002, the entire teachings of which are incorporated herein by reference.

The mobile cart 12 of FIG. 14 can optionally include a power supply, an x-ray power generator, and a computer system for controlling operation of the x-ray scanning device, including translational movement of the detector, and tilting movement of the x-ray source. The computer system can also perform various data processing functions, such as image processing, and storage of x-ray images. The mobile cart 12 preferably also includes a display system 60, such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system. It will be understood that one or more fixed units can also perform any of the functions of the mobile cart 12.

The O-shaped gantry can include a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, now U.S. Pat. No. 6,940,941, issued Sep. 6, 2005, the entire teachings of which are incorporated herein by reference.

It will also be understood that although the embodiments shown here include x-ray imaging devices having O-shaped gantries, other gantry configurations could be employed, including broken ring shaped gantries having less than full 360 degree rotational capability.

Figure 15:
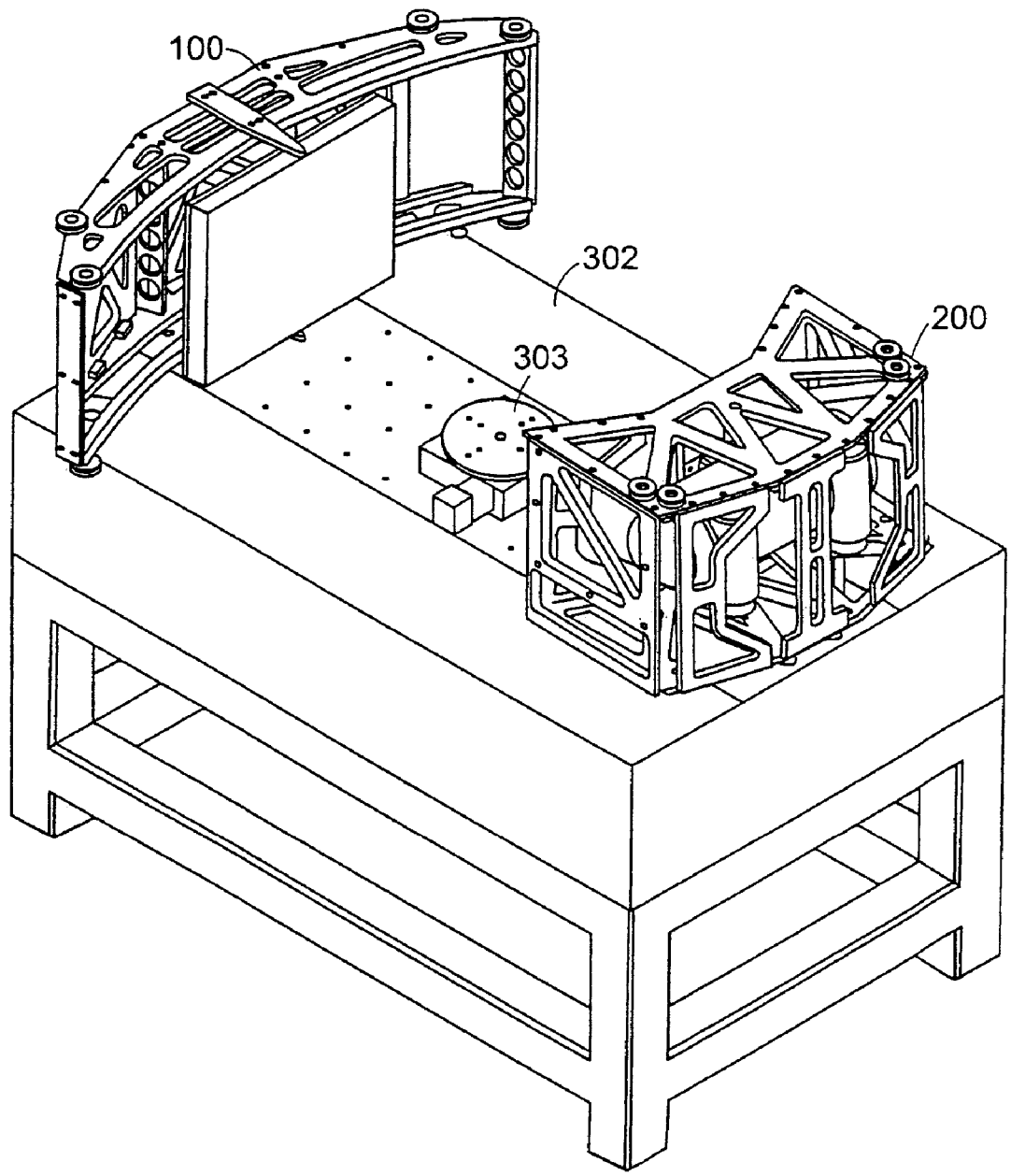
FIG. 15 illustrates a table-top x-ray assembly with rotatable stage for tomographic and planar imaging of large field-of-view objects according to yet another embodiment.

Referring to FIG. 15, a table-top version of the large field-of-view scanning device is depicted. In this embodiment, the connector bracket, gantry, and rotor friction drive have been replaced by a rigid table mount 302 and a turntable 303 located in the center of the field of view. The turntable rotates the object to be imaged in a complete 360-degree rotation to capture projection images from any direction. The detector and source positioning assemblies 100, 200 are rigidly mounted a fixed distance from one another. The turntable 303 can be rigidly mounted to the table at any point along the ray connecting the x-ray focal spot and the center of the detector positioning assembly. The data collection techniques for this embodiment are essentially the same as those described for the x-ray gantry, except that in this case, it is the rotation of the object relative to the source and detector, rather than the rotation of the source and detector relative to the object, which effects the x-ray scanning.

The x-ray imaging systems and methods described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques. This invention could be used for acquiring multi-planar x-ray images in a quasi-simultaneous manner, such as described in commonly-owned application entitled "Systems and Methods for Quasi-Simultaneous Multi-Planar X-Ray Imaging,", filed on Mar. 13, 2003, the entire teachings of which are incorporated herein by reference. Also, the images acquired at each detector position could be reprojected onto virtual equilinear or equiangular detector arrays prior to performing standard filtered backprojection tomographic reconstruction techniques, as described in commonly-owned U.S. Provisional Application No. 60/405,096, filed on Aug. 21, 2002.

The detector arrays described herein include two-dimensional flat panel solid-state detector arrays. It will be understood, however, that various detectors and detector arrays can be used in this invention, including any detector configurations used in typical diagnostic fan-beam or cone-beam imaging systems, such as C-arm fluoroscopes. A preferred detector is a two-dimensional thin-film transistor x-ray detector using scintillator amorphous-silicon technology.

While this invention has been particularly shown and described with references to preferred embodiments thereof, it will be understood by those skilled in the art that various changes in form and details may be made therein without departing from the scope of the invention encompassed by the appended claims. For instance, although the particular embodiments shown and described herein relate in general to computed tomography (CT) x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

What is claimed is:

1. An imaging apparatus, comprising:
   a source that projects a beam of radiation in a first trajectory;
   a detector located a distance from the source and positioned to receive the beam of radiation in the first trajectory;
   an imaging area between the source and the detector, the radiation beam from the source passing through a portion of the imaging area before it is received at the detector;
   a detector positioner that translates the detector to a second position in a direction that is substantially normal to the first trajectory; the detector positioner translating the detector relative to a stationary focal spot of the source;
   a beam positioner operable to pivot the radiation beam about the stationary focal spot so as to alter the trajectory of the radiation beam to direct the beam onto the detector located at the second position and;
   a gantry, the detector being translated within the gantry.

2. The apparatus of claim 1, wherein the detector is translated along an arc.

3. The apparatus of claim 1, wherein the detector is translated along a line.

4. The apparatus of claim 1, wherein the detector is a two-dimensional detector.

5. The apparatus of claim 4, wherein the detector is a two-dimensional flat panel detector array.

6. The apparatus of claim 1, wherein the source is an x-ray source.

7. The apparatus of claim 1, wherein the imaging area is configured to receive an object to be imaged, the object being more extensive than the field-of-view of the detector in at least one direction in which the detector is translatable.

8. The apparatus of claim 1, wherein the detector positioner comprises a positioner frame and a motor that translates the detector within the positioner frame.

9. The apparatus of claim 1, wherein the detector positioner comprises a rail and at least one bearing that mates with the rail to guide the detector as it translates.

10. The apparatus of claim 1, further comprising a positioning feedback system that indicates the position of the detector as it translates.

11. The apparatus of claim 10, wherein the positioning feedback system comprises a linear encoder tape and a read head.

12. The apparatus of claim 10, wherein the positioning feedback system comprises a rotary encoder and a friction wheel.

13. The apparatus of claim 1, wherein the detector translates along an arc whose radius is centered on the focal spot of the source.

14. The apparatus of claim 1, wherein the beam positioner directs the beam so that a central ray of the beam remains directed at the geometric center of the detector while the detector translates.

15. The apparatus of claim 1, wherein the beam positioner comprises a tilt system that tilts the source.

16. The apparatus of claim 15, wherein the tilt system tilts the source about its focal spot.

17. A method of imaging an object, comprising:
projecting a beam of radiation in a first trajectory, the beam traveling through a first region of the object and onto a detector located at a first position;
translating the detector to a second position in a direction that is substantially normal to the first trajectory, the detector translating within a gantry and relative to a stationary focal spot of the beam of radiation; and
pivoting the radiation beam about a stationary focal spot to alter the trajectory of the beam so that the beam travels through a second region of the object and onto the detector located at the second position.

* * * * *

(12) EX PARTE REEXAMINATION CERTIFICATE (8889th)
United States Patent
Gregerson et al.

(10) Number: US 7,661,881 C1
(45) Certificate Issued: *Mar. 6, 2012

(54) SYSTEMS AND METHODS FOR IMAGING LARGE FIELD-OF-VIEW OBJECTS

(75) Inventors: Eugene A. Gregerson, Bolton, MA (US); Richard K. Grant, Sudbury, MA (US); Norbert Johnson, North Andover, MA (US)

(73) Assignee: Medtronic Navigation, Inc., Minneapolis, MN (US)

Reexamination Request:
No. 90/011,750, Jun. 17, 2011

Reexamination Certificate for:
Patent No.: 7,661,881
Issued: Feb. 16, 2010
Appl. No.: 11/522,794
Filed: Sep. 18, 2006

( * ) Notice: This patent is subject to a terminal disclaimer.

Related U.S. Application Data

(63) Continuation of application No. 10/392,365, filed on Mar. 18, 2003, now Pat. No. 7,108,421.
(60) Provisional application No. 60/366,062, filed on Mar. 19, 2002.

(51) Int. Cl.
*H05G 1/04* (2006.01)

(52) U.S. Cl. ........................................ 378/197; 378/196
(58) Field of Classification Search .......................... None
See application file for complete search history.

(56) References Cited

To view the complete listing of prior art documents cited during the proceeding for Reexamination Control Number 90/011,750, please refer to the USPTO's public Patent Application Information Retrieval (PAIR) system under the Display References tab.

*Primary Examiner* — Christina Y Leung

(57) ABSTRACT

An imaging apparatus and related method comprising a source that projects a beam of radiation in a first trajectory; a detector located a distance from the source and positioned to receive the beam of radiation in the first trajectory; an imaging area between the source and the detector, the radiation beam from the source passing through a portion of the imaging area before it is received at the detector, a detector positioner that translates the detector to a second position in a first direction that is substantially normal to the first trajectory; and a beam positioner that alters the trajectory of the radiation beam to direct the beam onto the detector located at the second position. The radiation source can be an x-ray cone-beam source, and the detector can be a two-dimensional flat-panel detector array. The invention can be used to image objects larger than the field-of-view of the detector by translating the detector array to multiple positions, and obtaining images at each position, resulting in an effectively large field-of-view using only a single detector array having a relatively small size. A beam positioner permits the trajectory of the beam to follow the path of the translating detector, which permits safer and more efficient dose utilization, as generally only the region of the target object that is within the field-of-view of the detector at any given time will be exposed to potentially harmful radiation.

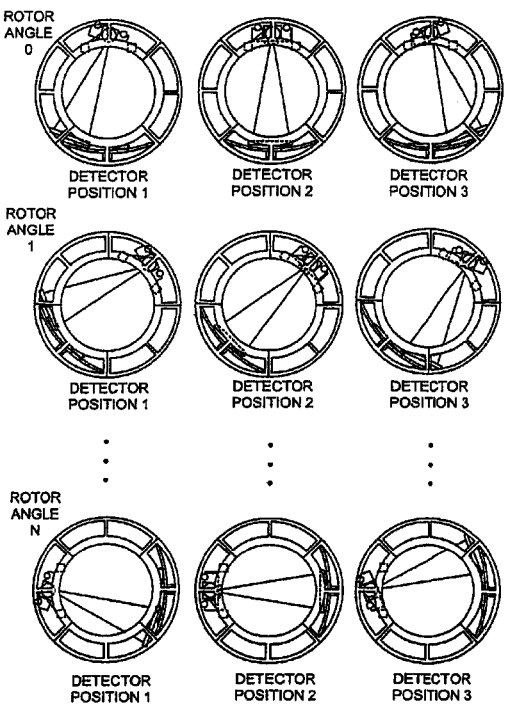

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8, 9 and 17 are cancelled.

Claim 1 is determined to be patentable as amended.

Claims 2-7 and 10-16, dependent on an amended claim, are determined to be patentable.

New claims 18 and 19 are added and determined to be patentable.

1. An imaging apparatus, comprising:
   a source that projects a beam of radiation in a first trajectory;
   a detector located a distance from the source and positioned to receive the beam of radiation in the first trajectory;
   an imaging area between the source and the detector, the radiation beam from the source passing through a portion of the imaging area before it is received at the detector;
   a detector positioner that translates the detector to a second position in a direction that is substantially normal to the first trajectory; the detector positioner translating the detector relative to a stationary focal spot of the source; *wherein the detector positioner comprises a positioner frame and a motor that translates the detector within the positioner frame;*
   a beam positioner operable to pivot the radiation beam about the stationary focal spot so as to alter the trajectory of the radiation beam to direct the beam onto the detector located at the second position and;
   a gantry, the detector being translated within the gantry.

*18. An imaging apparatus, comprising:*
*a source that projects a beam of radiation in a first trajectory;*
*a detector located a distance from the source and positioned to receive the beam of radiation in the first trajectory;*
*an imaging area between the source and the detector, the radiation beam from the source passing through a portion of the imaging area before it is received at the detector;*
*a detector positioner that translates the detector to a second position in a direction that is substantially normal to the first trajectory; the detector positioner translating the detector relative to a stationary focal spot of the source;*
*a beam positioner operable to pivot the radiation beam about the stationary focal spot so as to alter the trajectory of the radiation beam to direct the beam onto the detector located at the second position;*
*a gantry, the detector being translated within the gantry; and*
*a positioning feedback system that indicates the position of the detector as it translates, wherein the positioning feedback system comprises a rotary encoder and a friction wheel.*

*19. An imaging apparatus, comprising:*
*a source that projects a beam of radiation in a first trajectory;*
*a detector located a distance from the source and positioned to receive the beam of radiation in the first trajectory;*
*an imaging area between the source and the detector, the radiation beam from the source passing through a portion of the imaging area before it is received at the detector;*
*a detector positioner that translates the detector to a second position in a direction that is substantially normal to the first trajectory; the detector positioner translating the detector relative to a stationary focal spot of the source; wherein the detector positioner comprises a rail and at least one bearing that mates with the rail to guide the detector as it translates;*
*a beam positioner operable to pivot the radiation beam about the stationary focal spot so as to alter the trajectory of the radiation beam to direct the beam onto the detector located at the second position and;*
*a gantry, the detector being translated within the gantry.*

* * * * *